United States Patent
Gibson et al.

(10) Patent No.: US 7,264,792 B2
(45) Date of Patent: Sep. 4, 2007

(54) SOLID PHASE PREPARATION OF $^{18}$F-LABELLED AMINO ACIDS

(75) Inventors: Alexander Mark Gibson, Amersham (GB); Lynda Jane Brown, Southampton (GB); Richard Charles Downie Brown, Southampton (GB)

(73) Assignee: GE Healthcare Limited, Buckinghamshire (GB)

( * ) Notice: Subject to any disclaimer, the term of this patent is extended or adjusted under 35 U.S.C. 154(b) by 0 days.

(21) Appl. No.: 10/539,165

(22) PCT Filed: Dec. 19, 2003

(86) PCT No.: PCT/GB03/05576

§ 371 (c)(1), (2), (4) Date: Jun. 15, 2005

(87) PCT Pub. No.: WO2004/056725

PCT Pub. Date: Jul. 8, 2004

(65) Prior Publication Data

US 2006/0039855 A1    Feb. 23, 2006

(30) Foreign Application Priority Data

Dec. 20, 2002  (GB)  ................. 0229695.2

(51) Int. Cl.
  *A61M 36/14*  (2006.01)
  *C07F 5/00*  (2006.01)

(52) U.S. Cl. ....................... 424/1.89; 534/11

(58) Field of Classification Search ........... 534/11; 424/1.89
See application file for complete search history.

(56) References Cited

U.S. PATENT DOCUMENTS 5,808,146 A   9/1998  Goodman

FOREIGN PATENT DOCUMENTS

WO   97/17092   5/1997
WO   WO 03/002157 A1 *   1/2003

OTHER PUBLICATIONS

Chemical Abstract AN 1988:130967 of J. of Labelled Compounds and Radiopharm. (1987), vol. 24(9), pp. 1029-1042.
Martarello—Journal of Medicinal Chemistry (2002), vol. 45, pp. 2250-2259, in particular scheme 3.
Shoup—Journal of labeled Compounds and Radiopharmaceuticals (1999), vol. 42, pp. 215-225, in particular the final step in fig. 1.
Shoup—Journal of Nuclear Med., vol. 40, No. 2, 1999, pp. 331-338.
Search Report of GB 0229695.2 dated May 30, 2003.
Int'l Search Report for PCT/GB2003/005576 dated May 3, 2004.
Int'l Preliminary Exam Report for PCT/GB2003/005576 dated Sep. 27, 2004.

* cited by examiner

*Primary Examiner*—Michael G. Hartley
*Assistant Examiner*—Melissa Perreira
(74) *Attorney, Agent, or Firm*—Li Cai

(57) ABSTRACT

A process for the production of an $^{18}$F-labelled tracer which comprises treatment of a solid support-bound precursor of formula (I): SOLID SUPPORT-LINKER-SO$_2$—O-TRACER (I) with $^{18}$F— to produce the labelled tracer of formula (II)

$$^{18}F-R^1-CH_2 \diagdown C \diagup COP^1 \atop R^2-C_yH_z \diagup \diagdown NP^2P^3 \qquad (II)$$

13 Claims, No Drawings

SOLID PHASE PREPARATION OF $^{18}$F-LABELLED AMINO ACIDS

This application is a filing under 35 U.S.C. 371 of international application number PCT/GB2003/005576, filed Dec. 19, 2003, which claims priority to application number 0229695.2 filed Dec. 20, 2002, in Great Britain the entire disclosure of which is hereby incorporated by reference.

The present invention relates to novel solid-phase processes for the production of radiolabelled tracers, in particular for the production of $^{18}$F-labelled amino acids which may be suitable for use as Positron Emission Tomography (PET) radiotracers. The invention also comprises radiopharmaceutical kits using these novel processes.

The favoured radioisotope for PET, $^{18}$F, has a relatively short half-life of 110 minutes. $^{18}$F-labelled tracers for PET therefore have to be synthesised and purified as rapidly as possible, and ideally within one hour of clinical use. Standard synthetic methods for introducing fluorine-18 are relatively slow and require post-reaction purification (for example, by HPLC) which means that it is difficult to obtain the $^{18}$F-labelled tracer for clinical use in good radiochemical yield. There is also a need for automation to protect the operator from radiation exposure. Many radiofluorinations are complicated procedures and it is necessary to simplify them to facilitate automation.

The present invention provides solid-phase processes for producing $^{18}$F-labelled amino acids quickly and with high specific activity yet avoiding time-consuming purification steps, such that the resultant $^{18}$F-labelled amino acid is suitable for use in PET. The solid-phase methods also lend themselves to automation with advantages of ease of production and greater throughput. The invention also comprises radiopharmaceutical kits which use such processes and thus provide the radiopharmacist or clinician with a convenient means of preparing an $^{18}$F-labelled amino acid.

$^{18}$F-labelled amino acids, useful for tumour imaging are described in U.S. Pat. No. 5,808,146, an especially preferred example of such an amino acid being [$^{18}$F]-1-amino-3-fluorocyclobutane-1-carboxylic acid ([$^{18}$F]-FACBC). Solid-phase nucleophilic fluorination methods are described in co-pending International Patent In a first aspect, the invention provides a process for the production of an $^{18}$F-labelled tracer which comprises treatment of a solid support-bound precursor of formula (I):

SOLID SUPPORT-LINKER-SO$_2$—O-TRACER  (I)

wherein the TRACER is of formula (A):

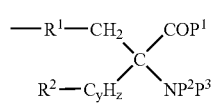

wherein P$^1$ is hydroxy or a protecting group, P$^2$ and P$^3$ are independently hydrogen or a protecting group, R$^1$ is a bond, —CH=CH—, or together with R$^2$ forms R$^3$;

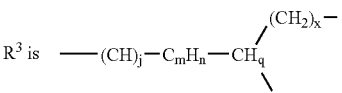

R$^2$ is hydrogen or together with R$^1$ forms R$^3$;
such that

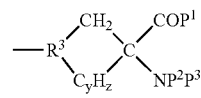

is formed
wherein x is 0 or 1;
y is 1 or 2;
z is 1, 2, 3, or 4 and z>y if y is 2;
q is 1 or 0 if n is 1 and j is 0;
n is 1 or 2, but 0 if m is 0;
m is 0 or 1; and
j is 0 or 1;
with $^{18}$F$^-$ to produce the labelled tracer of formula (II)

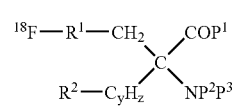

wherein R$^1$, R$^2$, y, z, P$^1$, P$^2$ and P$^3$ are as defined for the compound of formula (I), optionally followed by
(i) removal of excess $^{18}$F$^-$, for example by ion-exchange chromatography; and/or
(ii) removal of any protecting groups; and/or
(iii) removal of organic solvent; and/or
(iv) formulation of the resultant compound of formula (II) as an aqueous solution Preferably, in the compounds of formula (I) above, R$^1$ and R$^2$ form the group R$^3$, and more preferably, x is 0, y is 1, z is 2, q is 1, m is 0 and j is 0.

As the $^{18}$F-labelled tracer of formula (II) is removed from the solid-phase into solution, all unreacted precursor remains bound to the resin and can be separated by simple filtration, thus obviating the need for complicated purification, for example by HPLC. The $^{18}$F-labelled tracer of formula (II) may be cleaned up by removal of excess F$^-$, for example by ion-exchange chromatography and/or by removal of any organic solvent, for example by evaporation. Any protecting groups may be removed, and other simple processing steps such as passing through a C$_{18}$ purification column or evaporation may be performed. The resultant $^{18}$F-labelled tracer of formula (II) may then be further made-up into an aqueous formulation for clinical use.

As shown in Scheme 1, the compound of formula (I) may be conveniently prepared from any suitable commercially available resin, such as Merrifield Resin, NovaSyn® TG Bromo Resin, (Bromomethyl)phenoxymethyl polystyrene, or Wang Resin which may be reacted with a compound (the LINKER) that is functionalised with a sulphonyl fluoride or sulphonyl chloride at one end and with a reactive functionalisation, for example, a carboxylic acid, at the other end. This may be carried out by treating an amine functionalised resin with a linker compound having both a sulphonyl fluoride and an acid chloride functionality, in an appropriate inert solvent such as dichloromethane, chloroform, or acetonitrile, and heating at elevated temperature for a period of time. The excess reagent may then be removed from the resin by washing with further portions of the inert solvent. The sulphonyl chloride resin may then be reacted with the alcohol analogue of the tracer to produce the resin-bound precursor of formula (I). This may be carried out by treating the resin with a solution of the alcohol in an inert solvent such as chloroform, dichloromethane, acetonitrile, dioxane, or tetrahydrofuran containing a non-nucleophilic soluble base such as sodium hydride or a trialkylamine, for example triethylamine or diisopropylethylamine. The reaction may be carried out at a temperature of 10 to 80° C., optimally at ambient temperature for a period of from around 1 to 72 hours. The excess alcohol and base may then be removed from the solid support by washing with further portions of an inert solvent such as chloroform, dichloromethane or tetrahydrofuran. Alternatively, the LINKER may be bonded to the TRACER before attaching to the SOLID SUPPORT to form the compound of formula (I), using analogous chemistry to that described above.

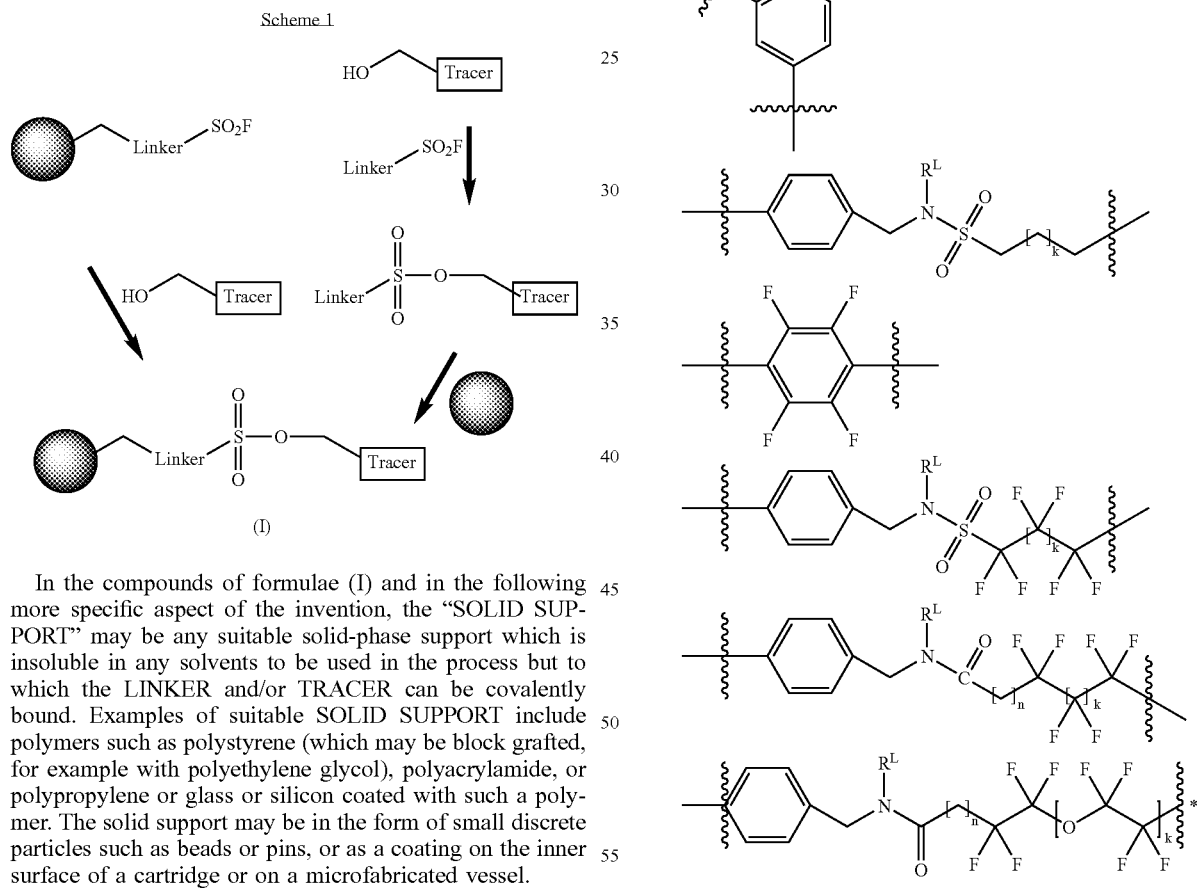

In the compounds of formulae (I) and in the following more specific aspect of the invention, the "SOLID SUPPORT" may be any suitable solid-phase support which is insoluble in any solvents to be used in the process but to which the LINKER and/or TRACER can be covalently bound. Examples of suitable SOLID SUPPORT include polymers such as polystyrene (which may be block grafted, for example with polyethylene glycol), polyacrylamide, or polypropylene or glass or silicon coated with such a polymer. The solid support may be in the form of small discrete particles such as beads or pins, or as a coating on the inner surface of a cartridge or on a microfabricated vessel.

In the compounds of formulae (I) and in the following more specific aspect of the invention, the "LINKER" may be any suitable organic group which serves to space the reactive site sufficiently from the solid support structure so as to maximise reactivity. Suitably, the LINKER comprises zero to four aryl groups (suitably phenyl) and/or a $C_{1-16}$alkyl (suitably $C_{1-6}$alkyl) or $C_{1-16}$haloalkyl (suitably $C_{1-6}$haloalkyl), typically $C_{1-16}$ fluoroalkyl (suitably $C_{1-6}$ fluoroalkyl), or $C_{1-16}$alkoxy or $C_{1-16}$haloalkoxy (suitably $C_{1-6}$alkoxy or $C_{1-16}$haloalkoxy) typically $C_{1-6}$fluoroalkoxy (suitably $C_{1-6}$fluoroalkoxy), and optionally one to four additional functional groups such as amide or sulphonamide groups. Examples of such linkers are well known to those skilled in the art of solid-phase chemistry, but include:

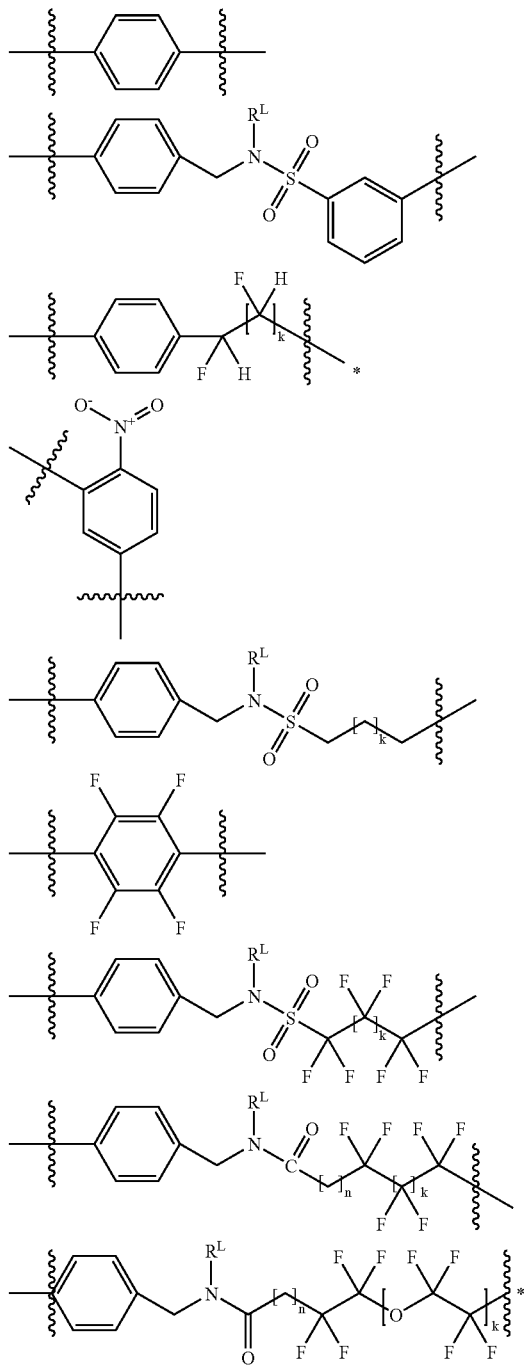

wherein at each occurrence, k is an integer of 0 to 3, n is an integer of 1 to 16, and $R^L$ is hydrogen or $C_{1-6}$ alkyl.

As would be apparent to the person skilled in the art, it may be necessary to protect functional groups in the TRACER to avoid unwanted reactions during the radiolabelling process. Such protection may be achieved using standard methods of protecting group chemistry. After the radiolabelling is complete, any protecting groups may be removed by simple procedures which are also standard in the art. Suitable protection and deprotection methodologies may be found, for example, in Protecting Groups in Organic Synthesis, Theodora W. Greene and Peter G. M. Wuts, published by John Wiley & Sons Inc. Preferred carboxylic acid protecting groups, $P^1$, include $C_{1-6}$ alkyl esters. Preferred amine protecting groups $P^2$ and $P^3$ include butoxycarbonyl, formamide, tosylate, fluorenylmethoxy carbonyl, trifluoroacetamide, succinimide, and phthalimide.

Treatment of the compound of formula (I) with $^{18}F^-$ may be effected by treatment with any suitable source of $^{18}F^-$, such as $Na^{18}F$, $K^{18}F$, $Cs^{18}F$, tetraalkylammonium $^8F$ fluoride, or tetraalkylphosphonium $^{18}F$ fluoride. To increase the reactivity of the fluoride, a phase transfer catalyst such as 4,7,13,16,21,24 hexaoxa-1,10-diazabicyclo[8,8,8]hexacosane may be added and the reaction performed in a non protic solvent. These conditions give reactive fluoride ions. The treatment with $^{18}F^-$ is suitably effected in the presence of a suitable organic solvent such as acetonitrile, dimethylformamide, dimethylsulphoxide, tetrahydrofuran, dioxan, 1,2 dimethoxyethane, sulpholane, N-methylpyrolidinineone, at a non-extreme temperature, for example, 15° C. to 180° C., preferably at elevated temperature. On completion of the reaction, the $^{18}F$-labelled tracer of formula (II) dissolved in the solvent is conveniently separated from the solid-phase by filtration. The same fluorination techniques may be used in the following more specific aspects of the invention.

Any excess $^{18}F^-$ may be removed from the solution of $^{18}F$-tracer by any suitable means, for example by ion-exchange chromatography or solid phase absorbents. Suitable ion-exchange resins include BIO-RAD AG 1-X8 or Waters QMA and suitable solid phase absorbents include alumina. The excess $^{18}F^-$ may be removed using such solid phases at room temperature in aprotic solvents.

Any organic solvent may be removed by any standard method such as by evaporation at elevated temperature in vacuo or by passing a stream of inert gas such as nitrogen or argon over the solution.

Before use of the $^{18}F$-labelled tracer, it may be appropriate to formulate it, for example as an aqueous solution by dissolving the $^{18}F$-labelled tracer in sterile isotonic saline which may contain up to 10% of a suitable organic solvent such as ethanol, or a suitable buffered solution such as a phosphate buffer. Other additives may be added such as ascorbic acid to reduce radiolysis.

In a preferred aspect, the present invention provides, a process for the production of [$^{18}F$]-1-amino-3-fluorocyclobutane-1-carboxylic acid ([$^{18}F$]-FACBC) which comprises treatment of a solid support-bound precursor of formula (Ia):

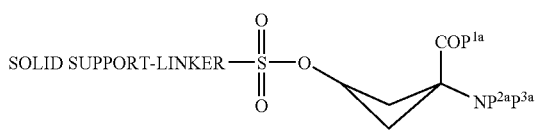

(Ia)

wherein $P^{2a}$ and $P^{3a}$ are each independently hydrogen or a protecting group, and $P^{1a}$ is hydroxyl or a protecting group; with $^{18}F^-$ to produce the labelled tracer of formula (IIa):

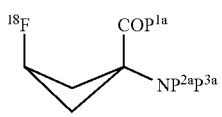

(IIa)

wherein $P^{1a}$, $P^{2a}$, and $P^{3a}$ are each as defined in Formula (Ia); optionally followed by
(i) removal of excess $^{18}F^-$, for example by ion-exchange chromatography; and/or
(ii) removal of the protecting groups; and/or
(iii) removal of organic solvent; and/or
(iv) formulation of the resultant compound of formula (IIa) as an aqueous solution.

In the compound of formula (Ia) the LINKER is preferably

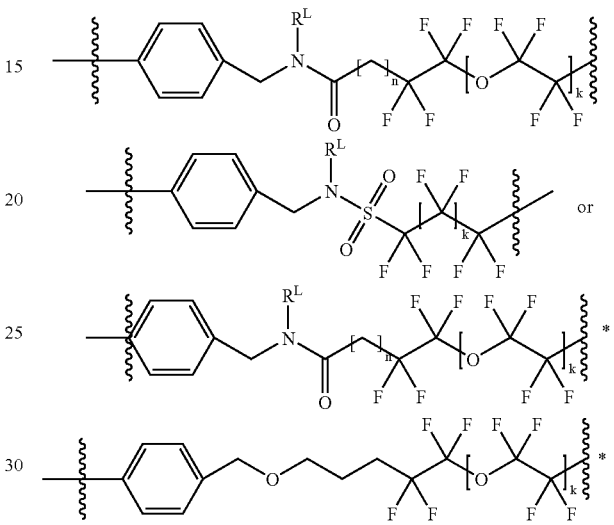

wherein $R^L$ is hydrogen or $C_{1-6}$-alkyl, n is 1 to 16, and k is 0 to 3.

and the SOLID SUPPORT is suitably a polystyrene resin.

Removal of any protecting groups from the compound of formula (IIa) may be effected by standard methods as referred to above. In a preferred embodiment of this aspect of the invention, the carboxylic acid groups are protected as esters, suitably $C_{1-6}$ alkanoic esters, preferably as acetate esters, and the amine groups may be protected with an $C_{1-6}$ alkoxy carbonyl, preferably t-butoxycarbonyl group. Such protecting groups may be conveniently removed by hydrolysis, for example in the presence of acid or base. Such deprotection may be effected on using solid supported acid or base catalysts that render the need for post deprotection neutralisation unnecessary The compounds of formula (I) and (Ia) are novel and thus form a further aspect of the present invention.

As described above, the advantages of such solid-phase processes for preparation of $^{18}F$-labelled tracers include the relative speed of the process, simplified purification methods and ease of automation-all of which mean that the processes are suitable for preparation of $^{18}F$-labelled tracers for use in PET. Accordingly, the present invention provides the a process for the production of a $^{18}F$-labelled tracer of formula (II) or (IIa) for use in PET.

Conveniently, the solid support bound precursor of formula (I) or (Ia) could be provided as part of a kit to a radiopharmacy. The kit may contain a cartridge which can be plugged into a suitably adapted automated synthesiser. The cartridge may contain, apart from the solid support-bound precursor, a column to remove unwanted fluoride ion, and an appropriate vessel connected so as to allow the reaction mixture to be evaporated and allow the product to be formulated as required. The reagents and solvents and other consumables required for the synthesis may also be included together with a compact disc carrying the software which allows the synthesiser to be operated in a way so as to meet the customers requirements for radioactive concentration, volumes, time of delivery etc.

Conveniently, all components of the kit are disposable to minimise the possibilities of contamination between runs and may be sterile and quality assured.

The invention further provides a radiopharmaceutical kit for the preparation of an $^{18}$F-labelled tracer for use in PET, which comprises:
(i) a vessel containing a compound of formula (I) or (Ia); and
(ii) means for eluting the vessel with a source of $^{18}$F$^-$;
(iii) an ion-exchange cartridge for removal of excess $^{18}$F$^-$; and optionally
(iv) a cartridge for solid-phase deprotection of the resultant product of formula (II) or (IIa).

The invention further provides a cartridge for a radiopharmaceutical kit for the preparation of an $^{18}$F-labelled tracer for use in PET which comprises:
(i) a vessel containing a compound of formula (I) or (Ia); and
(ii) means for eluting the vessel with a source of $^{18}$F$^-$.

The invention will now be illustrated by way of the following Examples. Throughout the Examples, abbreviations used are as follows:
DCM: dichloromethane
DMF: N, N-dimethylformamide
DIPEA: Diisopropylethylamine
DPPCl: Diphenyl phosphorochloridate
w/v: weight/volume
h: hour(s)
tlc: thin layer chromatography
THF: tetrahydrofuran
eq.: equivalents

EXAMPLE 1

Synthesis of syn- and anti-1-amino-3-[$^{18}$F]-fluoro-cyclobutane-1-carboxylic acid (FACBC)

Intermediate 1

Preparation of 1-t-butyl carbamate-3-hydroxy-1-cyclobutane-1 carboxylic acid methyl ester

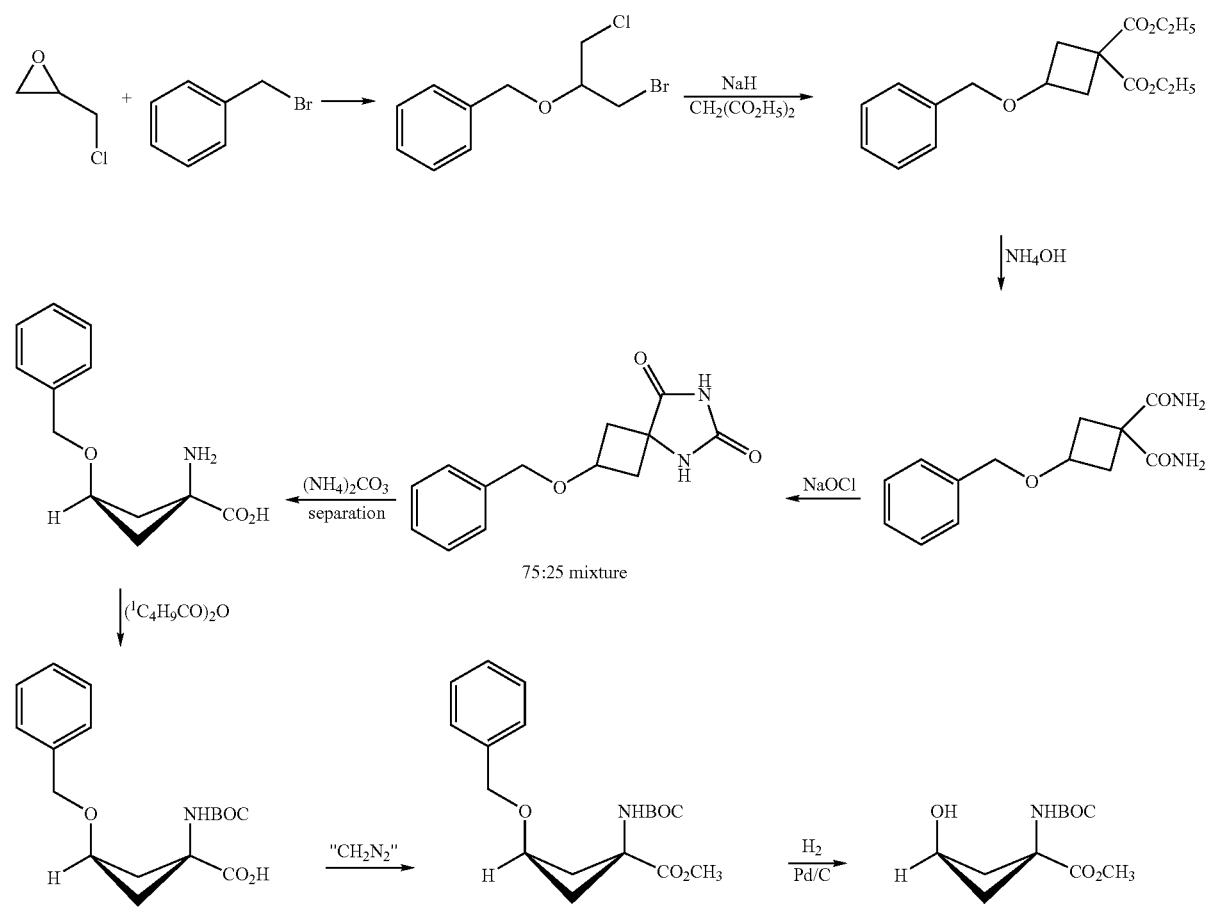

In a further aspect of the invention, there is provided a method for obtaining a diagnostic PET image which comprises the step of using a radiopharmaceutical kit or a cartridge for a radiopharmaceutical kit as described above.

Following literature Shoup, T. M. & Goodman, M. M. Journal of Labelled Compounds and Radiopharmaceuticals (1999), 42,215, the hydroxy intermediate is synthesised

EXAMPLE 1(i)

Synthesis of perfluoroalkyl sulphonyl Linker (D)

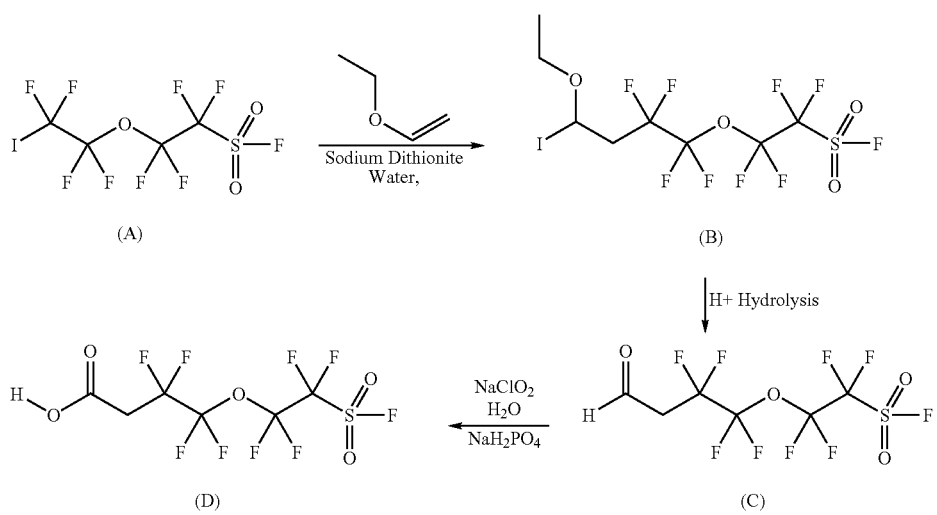

Following Yijun Pan and Christopher Holmes. A traceless Perfluoroalkylsulphonyl linker for the deoxygenation of phenols, Organic letters, July 2001, p83-86 and supplementary information attached.

To the solution of ethyl vinylether (600 mg, 8.3 mmol), NaHCO$_3$ (680 mg, 8.0 mmol), and Tetrafluoro-2-tetrafluoro-2-iodoethoxy) ethanesulphonyl fluoride (A) supplied by Apollo (3.5 g, 8.0 mmol) in CH$_3$CN (8 ml) and H$_2$O (7 ml) was slowly added Na$_2$S$_2$O$_4$ (1.64 g, 8.0 mmol) at 0° C. under stirring. The mixture was stirred at 5° C. for 50min. The pH of the reaction mixture was adjusted to 6.2~7.0 by adding 3N aqueous HCl and the mixture was stirred at 25° C. for another 20 min. It was extracted with CH$_2$Cl$_2$, washed with water and concentrated under reduced pressure. The oil residue was dissolved in acetone (38 ml) and the solution was added to a stirring mixture of 2-methyl-butene-2 (36 ml), NaH$_2$PO$_4$ (4.0 g, 30 mmol), NaClO$_2$ (5.0 g, 55 mmol) and water (40 ml) at 0-5° C. The reaction mixture was stirred at 10-15° C. for 2 h. It was concentrated under reduced pressure, extracted with ether, washed with brine, dried (Na$_2$SO$_4$) and concentrated for chromatography (CHCl$_3$/MeOH, 100:2) to afford compound (D) (866 mg, 30%). F-19 NMR; C-13 NMR

EXAMPLE 1(ii)

Synthesis of Acyl Chloride Linker (E)

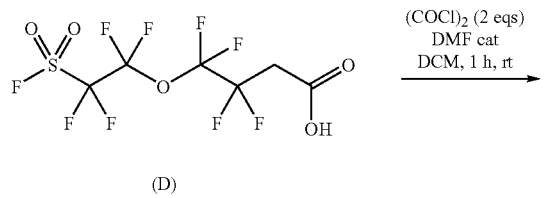

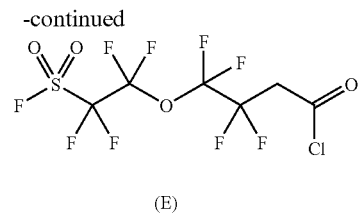

The acyl chloride (E) was prepared by adding 2 drops of dry DMF (Aldrich) to a dry DCM solution (4 mL; Aldrich)) of the corresponding acid (0.79 g, 2.2 mmol) and oxalyl chloride (0.38 mL, 4.4 mmol, Aldrich). Gas was released over ten minutes and the mixture stirred for 1 hour at room temperature. The resulting-solution was evaporated under reduced pressure and the residue dissolved in 2 mL of dry DCM.

EXAMPLE 1(iii)

Synthesis of PS-Resin Linker

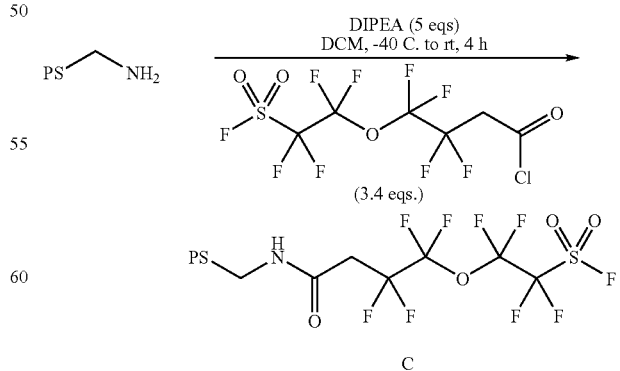

In an oven-dried Radleys reaction tube were placed 1 g of polystyrene resin (1 g, 1.30 mmol.g$^{-1}$, Novabiochem 01-64-0143, 100-200 mesh) and 16 mL of dry DCM (Aldrich). The tube was flushed with nitrogen and cooled to −40° C. A DCM (dry, Aldrich) solution of acyl chloride (D) (2 mL; 4.4 mmol; 3.4 eqs) was added followed by dry DIPEA (2.2 mmol; 5 eqs). The yellow reaction mixture became orange upon warming slowly to room temperature. After 5 hours, the resin was filtred of and washed thoroughly with DCM and methanol. The orange solid was evaporated under reduced pressure.

$^{19}$F NMR, δ(ppm, CDCl$_3$, reference CFCl$_3$, 282.65 MHz):45.1 (SO$_2$F), −82.6 (OCF$_2$), −87.9 (OCF$_2$), −112.6 (CF$_2$SO$_2$F), −115.7 (CF$_2$CH$_2$) ppm.

EXAMPLE 1(iv)

Synthesis of Solid Supported 1-t-butyl carbamate-1-cyclobutane-1 carboxylic acid methyl ester A portion of the resin prepared in the manner of Example 1(iii) above is swollen with dichloromethane (2 ml). To this resin is added a solution in dioxane of -t-butyl carbamate-3-hydroxy-1-cyclobutane-1 carboxylic acid methyl ester (Intermediate 1) which has been treated with sodium hydride to give the sodium salt. The suspension is stirred for 40 hours at 80° C. The suspension is then filtered and the resin is washed with THF

EXAMPLE 1(v)

Radiofluorination to Prepare [$^{18}$F]-FACBC

To a portion of the resin (prepared as described in Example 1(vii)) held in a cartridge is added a solution in dry acetonitrile of kryptofix, potassium carbonate and [$^{18}$F]-fluoride. The suspension is heated to 85° C. for 10 minutes and then the solution is filtered off. The solution is then passed onto a C$_{18}$ solid phase extraction cartridge and washed with water to remove acetonitrile, kryptofix and potassium carbonate. Addition of more acetonitrile washes the radiofluorinated product of the cartridge into a solution of 6 M HCl. This solution is heated for 5 minutes at 130° C. before neutralization and analysis.

EXAMPLE 2

Synthesis of syn- and anti-1-amino-3-[$^{18}$F]-fluoro-cyclobutane-1-carboxylic acid (FACBC)

2. (i)

Preparation of 1-t-butyl carbamate-3-hydroxy-1-cyclobutane-1 carboxylic acid methyl ester This step was performed as described above (Intermediate 1).

EXAMPLE 2(ii)

Synthesis of 1-tert-butoxycarbonylamino-3-[1,1,2,2-tetrafluoro-2-(1,1,2,2-tetrafluoro-2-iodoethoxy) ethanesulfonyloxy]-cyclobutane carboxylic acid methyl ester

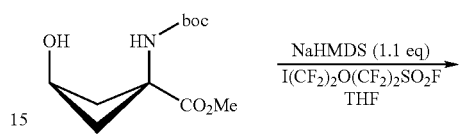

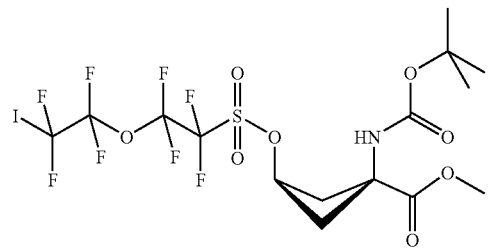

To the solution of 1-tert-butyl carbamate-3-hydroxy-1-cyclobutane-1 carboxylic acid methyl ester in THF at 0° C. was added 1.1 equivalents of sodium bis(trimethylsilyl) amide. After 30 minutes at 0° C. 1.1 equivalents of tetrafluoro-2-tetrafluoro-2-iodoethoxy) ethanesulfonyl fluoride was added. After 30 minutes the ice bath was removed and the mixture allowed to warm to ambient temperature. The solvent was removed at reduced pressure at room temperature. The crude mixture was purified by silica gel chromatography eluting with ethyl acetate/petroleum ether (3:7) yielding the desired product as an oil.

NMR (CDCl$_3$), δH: 1.44 (9H, s, Boc), 2.70-3.21 (4H, m, vbr, cyclobutane), 3.77 (3H, s, OMe), 5.41 (1H, p, J=7.2 Hz, 3C—H), δF: 118.3, 115.5, 82.6, 65.6

EXAMPLE 2(iii)

Synthesis of 1-tert-butoxycarbonylamino-3-[2-(12-carboxy-1,1,2,2-tetrafluoro-4-iodododecyloxy)-1,1,2,2fluoroethanesulfonyloxy]-cyclobutane carboxylic acid methyl ester

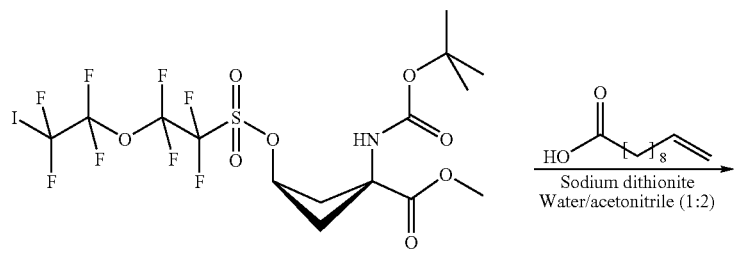

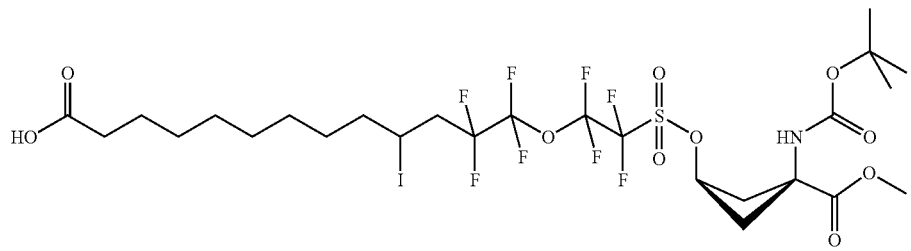

To the solution of 1-tert-butoxycarbonylamino-3-[1,1,2,2-tetrafluoro-2-(1,1,2,2-tetrafluoro-2-iodoethoxy)ethanesulfonyloxy]cyclobutane carboxylic acid methyl ester in water/acetonitrile (1:2) cooled in an ice/water bath was added sequentially 1.2 equivalent of sodium bicarbonate, 1.2 equivalent of sodium dithionite and 1 equivalent of undecylenic acid. The mixture was stirred for one hour and is allowed to warm to ambient temperature. The solvent was removed under reduced pressure at ambient temperature. The aqueous layer was extracted three times with ethyl acetate. The organic layer was dried over magnesium sulfate, filtered and the solvent removed at reduced pressure. The crude mixture was purified by silica gel chromatography eluting with ethyl acetate/petroleum ether (graduated form 0% to 90% ethyl acetate). NMR (CDCl$_3$), δH: 1.32 (10H, s, vbr), 1.44 (9H, s, vbr, BOC), 1.55-1.85 (4H, m, vbr), 2.35 (2H, t, 7.2Hz), 2.41-3.25 (5H, m, vbr), 3.81 (3H, s, OMe), 4.30 (1H, s, br, NH), 5.41 (1H, p, br, 3-CH)

EXAMPLE 2(iv)

Synthesis of 1-tert-butoxycarbonylamino-3-[2-(12-carboxy-1,1,2,2-tetrafluorododecyloxy)-1,1,2,2-tetrafluoroethanesulfonyloxy]-cyclobutane carboxylic acid methyl ester

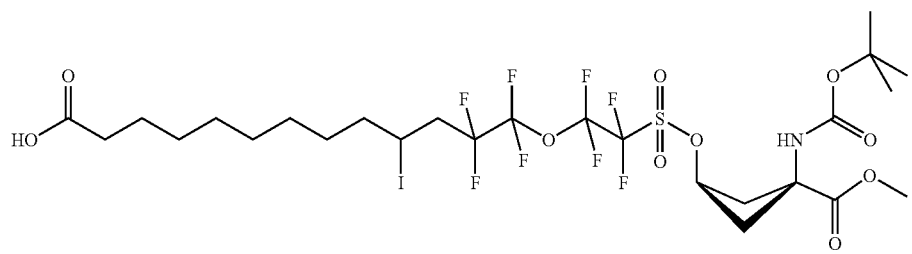

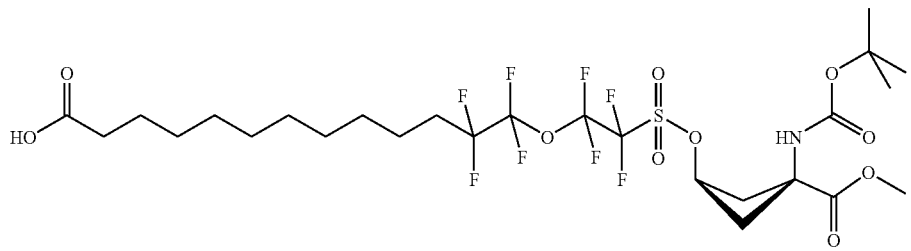

To the solution of 1-tert-butoxycarbonylamino-3-[2-(12-carboxy-1,1,2,2-tetrafluoro-4-iodododecyloxy)-1,1,2,2-tetrafluoroethanesulfonyloxy]-cyclobutane carboxylic acid methyl ester in diethyl ether was added an excess of zinc metal followed-by acetic acid. The mixture was heated at reflux for 1 hour. The mixture was cooled and the solvent decanted off taking care no zinc metal passed out of the reaction vessel. The solvent was removed at reduced pressure at ambient pressure.

EXAMPLE 2(v)

Solid support synthesis of 1-tert-butoxycarbonylamino-3-[2-(12-carboxy-1,1,2,2-tetrafluorododecyloxy)-1,1,2,2-tetrafluorododdecyloxy)-1,1,2,2-tetrafluoroethanesulfonyloxy]-cyclobutane carboxylic acid methyl ester

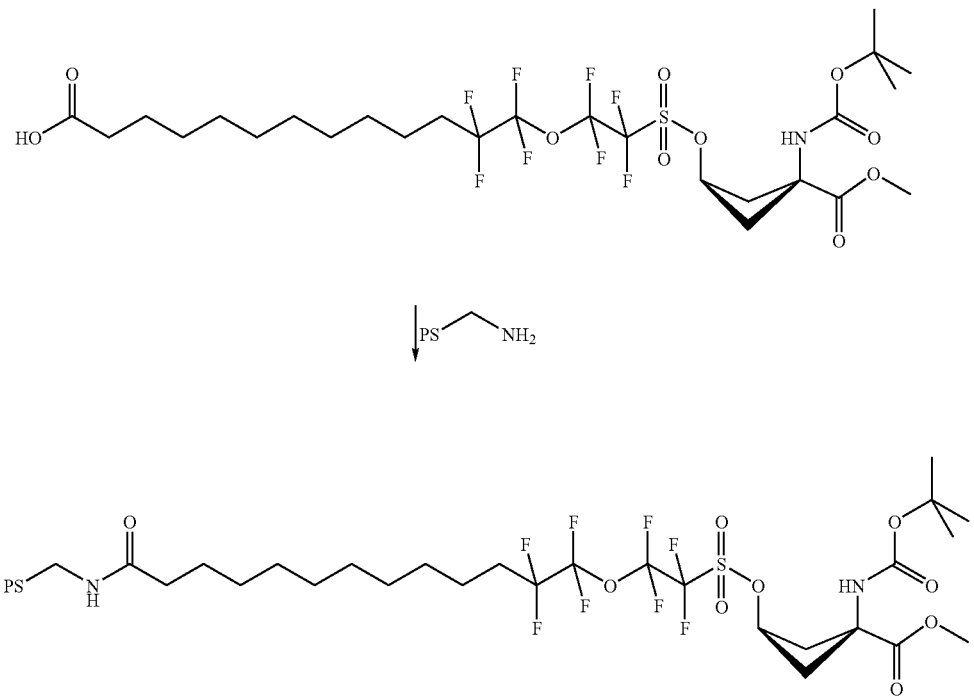

In an oven-dried Radleys reaction tube is placed 1 g of polystyrene resin (1 g, 1.30 mmol.g$^{-1}$, Novabiochem 01-64-0143, 100-200 mesh) and 16 mL of dry DCM (Aldrich). To this is added sequentially 1-tert-butoxycarbonylamino-3-[2-(12-carboxy-1,1,2,2-tetrafluorododecyloxy)-1,1,2,2-tetrafluoroethanesulfonyloxy]-cyclobutane carboxylic acid methyl ester (1.1 equivalent), Hunig's base (2.0 equivalent) and DPPCl (1.1 equivalent). After 5 hours the resin is filtered of and washed thoroughly with DCM and methanol. The solid is dried at reduced pressure.

EXAMPLE 2(vi)

Radiofluorination to prepare [$^{18}$F]-FACBC

To a portion of the resin (prepared as described in Example 2(v) held in a cartridge is added a solution in dry acetonitrile of kryptofix, potassium carbonate and [$^{18}$F]-fluoride. The suspension is heated to 85° C. for 10 minutes and then the solution is filtered off. The solution is then passed onto a C$_{18}$ solid phase extraction cartridge and washed with water to remove acetonitrile, kryptofix and potassium carbonate. Addition of more acetonitrile washes the radiofluorinated product of the cartridge into a solution of 6 M HCl. This solution is heated for 5 minutes at 130° C. before neutralization and analysis.

EXAMPLE 3

Synthesis of syn-and anti-1-amino-3-[$^{18}$F]-fluoromethyl-cyclobutane-1-carboxylic acid (FMACBC)

Intermediate 1

Preparation of 1-[N-(t-butoxycarbonyl)amino]-3-hydroxymethyl-1-cyclobutane-1-carboxylic acid t-butyl ester

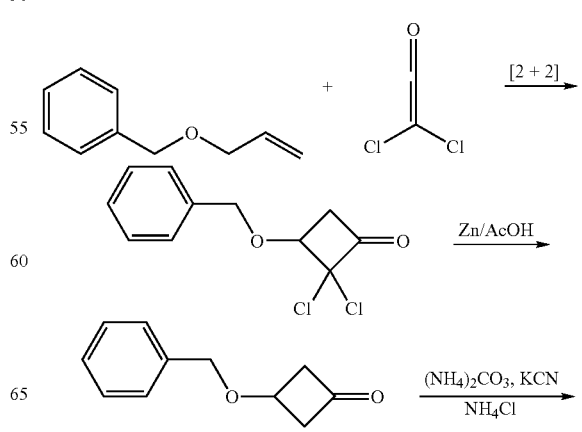

17

-continued

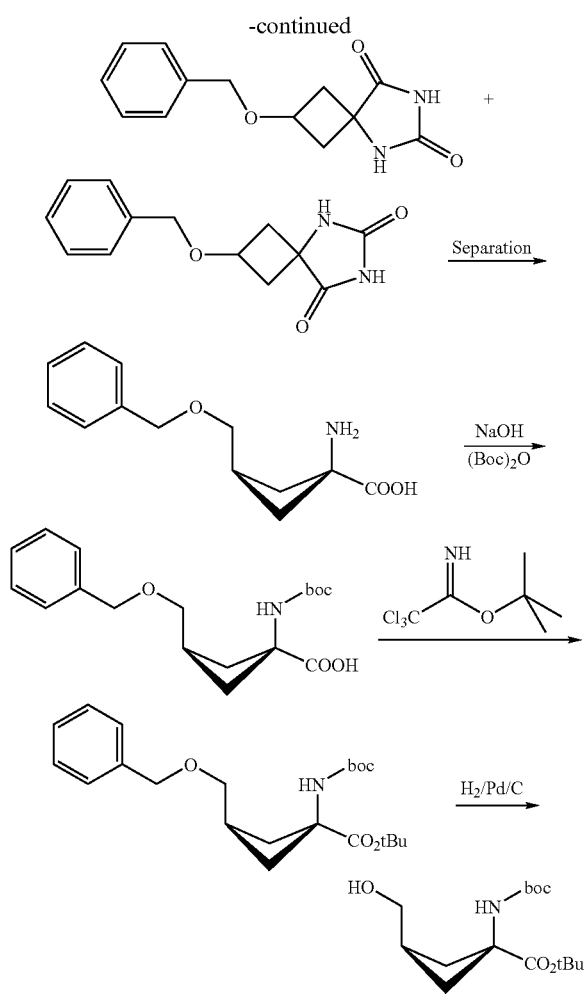

Following literature from Martarello, L., McConathyl, J., Camp, V. M., Malveaux, E. J., Simpson, N. E., Simpson, C. P., Olson, J. J., Bowers, G. D. and Goodman, M. M. Journal of Medicinal Chemistry 2002, 45, 2250, the hydroxymethyl intermediate is synthesised.

EXAMPLE 3(i)

Synthesis of solid supported 1-[N-(t-butoxycarbonyl)amino]-3-hydroxymethyl-1-cyclobutane-1-carboxylic acid t-butyl ester

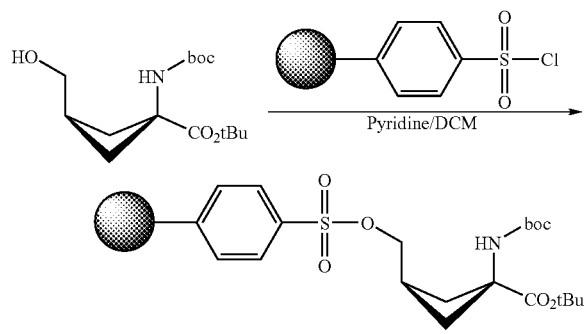

18

The resin is swelled in pyridine/DCM (1:1) and to this is added 1-[N-(t-butoxycarbonyl)amino]-3-hydroxymethyl-1-cyclobutane-1-carboxylic acid t-butyl ester. The reaction is monitored via a test for the complete consumption of the sulfonyl chloride: several beads are placed in a solution of 5% ethylenediamine in DMF for five minutes; these beads are then thoroughly washed (DMF×3, DCM×3, THF×3) and then is treated with a solution of 1% bromophenol blue in dimethylacetamine. The beads are then washed with DMF five times. Blue beads indicate the presence of sulfonyl chloride groups on the resin, but if the beads are white (or off white) the reaction has finished.

EXAMPLE 3(ii)

Preparation of [$^{19}$F]FMeACBC.

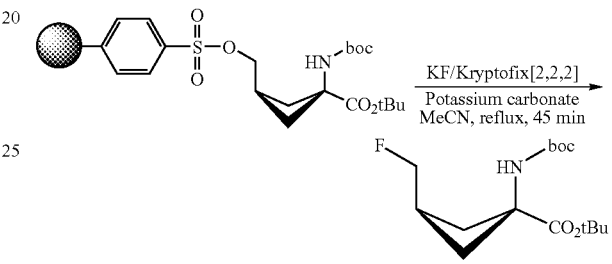

To the solid supported 1-[N-(t-butoxycarbonyl)amino]-3-hydroxymethyl-1-cyclobutane-1-carboxylic acid t-butyl ester in acetonitrile is added potassium fluoride, kryptofix [2,2,2] and potassium carbonate. The solution is heated at reflux for 45 minutes. The reaction mixture is allowed to cool to ambient temperature and then filtered, and washed with acetonitrile. The organic layer is collected. The solvent is removed at reduced pressure and this yields [$^{19}$F] FMeACBC. NMR (CDCl$_3$), δH: 1.37 (9H, s, (CH$_3$)$_3$C), 1.43 (9H, s, (CH$_3$)$_3$C), 2.16-2.34 (2H, s, br, CH$_2$), 2.45-2.57 (2H, m, br, CH$_2$), 4.34 (2H, d, J=7 HZ, CH$_2$F), 5.17 (1H, s, NH), δC: 28.0 (CH$_3$), 28.5 (CH$_3$), 33.3 (CH$_2$), 55.1 (C(NH)(C=O)), 79.7 (C(CH$_3$)$_3$), 81.7 (C(CH$_3$)$_3$), 85.2, 87.4 (CH$_2$F), 154.7 (C=O), 173.2 (C=O)

[$^{18}$F] FMeACBC may be prepared from the intermediate of Example 3(i) with analogous chemistry using [$^{18}$F] potassium fluoride.

The invention claimed is:

1. A process for the production of an $^{18}$F-labelled tracer which comprises treatment of a solid support-bound precursor of formula (I):

SOLID SUPPORT-LINKER-SO$_2$—O-TRACER    (I)

wherein the TRACER is of formula (A):

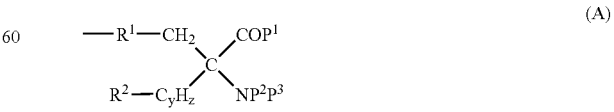

wherein P$^1$ is hydroxy or a protecting group, P$^2$ and P$^3$ are independently hydrogen or a protecting group, R$^1$ is a bond, —CH=CH—, or together with R$^2$ forms R$^3$;

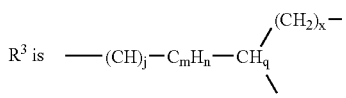

$R^2$ is hydrogen or together with $R^1$ forms $R^3$;
such that

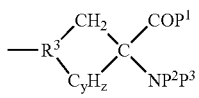

is formed
  wherein x is 0 or 1;
  y is 1 or 2;
  z is 1, 2, 3, or 4 and z>y if y is 2;
  q is 1 or 0 if n is 1 and j is 0;
  n is 1 or 2, but 0 if m is 0;
  m is 0 or 1; and
  j is 0 or 1;
with $^{18}F^-$ to produce the labelled tracer of formula (II)

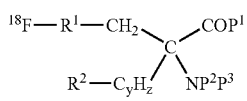 (II)

wherein $R^1$, $R^2$, y, z, $P^1$, $P^2$ and $P^3$ are as defined for the compound of formula (I), optionally followed by
  (i) removal of excess $^{18}F^-$, for example by ion-exchange chromatography; and/or
  (ii) removal of any protecting groups; and/or
  (iii) removal of organic solvent; and/or
  (iv) formulation of the resultant compound of formula (II) as an aqueous solution.

2. A process for the production of an $^{18}F$-labelled tracer according to claim 1 wherein $R^1$ and $R^2$ form the group $R^3$.

3. A process for the production of an $^{18}F$-labelled tracer according to claim 1 wherein $R^1$ and $R^2$ form the group $R^3$ and x is 0, y is 1, z is 2, q is 1, m is 0 and j is 0.

4. A process according to claim 1 for the production of [$^{18}F$]-1-amino-3-fluorocyclobutane-1-carboxylic acid ([$^{18}F$]-FACBC) which comprises treatment of a solid support-bound precursor of formula (Ia):

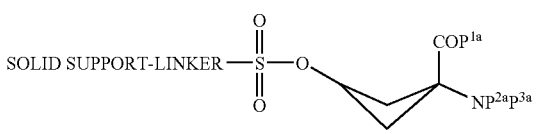 (Ia)

wherein $P^{2a}$ and $P^{3a}$ are each independently hydrogen or a protecting group, and $P^{1a}$ is hydroxyl or a carboxylic acid protecting group;

with $^{18}F$ to produce the labelled tracer of formula (IIa)

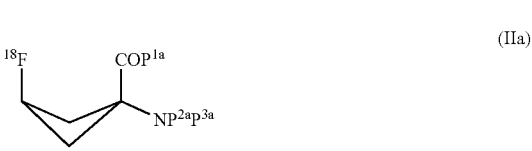 (IIa)

wherein $P^{1a}$, $P^{2a}$, $P^{3a}$ are each as defined in Formula (Ia); optionally followed by
  (i) removal of excess $^{18}F^-$, for example by ion-exchange chromatography; and/or
  (ii) removal of the protecting groups; and/or
  (iii) removal of organic solvent; and/or
  (iv) formulation of the resultant compound of formula (IIa) as an aqueous solution.

5. A process according to claim 4 wherein the LINKER in the compound of formula (Ia) is

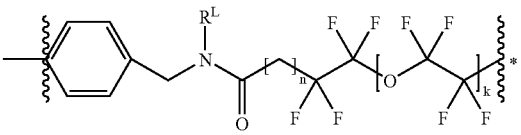

wherein k is an integer of 0 to 3, n is an integer of i to 16, and $R^L$ is hydrogen or $C_{1-6}$ alkyl.

6. A process according to claim 4 in which $P^{1a}$ is $C_{1-6}$alkoxy, $P^{2a}$ is hydrogen or $C^{1-6}$alkoxycarbonyl, and $P^{3a}$ is $C_{1-6}$alkoxycarbonyl.

7. A process for the production of a $^{18}F$-labelled tracer of formula (II), according to claim 1, for use in PET.

8. A compound of formula (I)

SOLID SUPPORT-LINKER-SO$_2$—O-TRACER  (I)

wherein the TRACER is of formula (A):

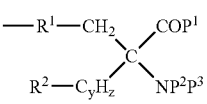 (A)

wherein $P^1$ is hydroxy or a protecting group, $P^2$ and $P^3$ are independently hydrogen or a protecting group, $R^1$ is a bond, —CH=CH—, or together with $R^2$ forms $R^3$;

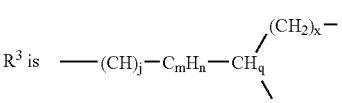

$R^2$ is hydrogen or together with $R^1$ forms $R^3$;
such that

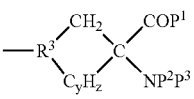

is formed
  wherein x is 0 or 1;
  y is 1 or 2;
  z is 1, 2, 3, or 4 and z>y if y is 2;
  q is 1 or 0 if n is 1 and j is 0;
  n is 1 or 2, but 0 if m is 0;
  m is 0 or 1; and
  j is 0 or 1.

9. A compound of formula (Ia):

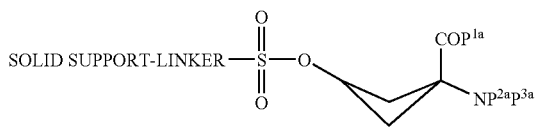

wherein $P^{2a}$ and $P^{3a}$ are each independently hydrogen or a protecting group, and $P^{1a}$ is hydroxyl or a protecting group.

10. A compound according to claim 8 in which the LiNKER is

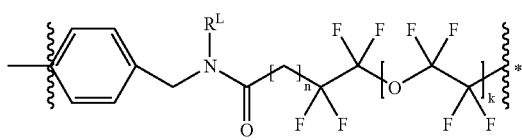

wherein k is an integer of 0 to 3, n is an integer of 1 to 16, and $R^L$ is hydrogen or $C_{1-6}$ alkyl.

11. A compound according to claim 9, in which $P^{1a}$ is $C^{1-6}$alkoxy, $P^{2a}$ is hydrogen or $C_{1-6}$alkoxycarbonyl, and $P^3a$ is $C^{1-6}$alkoxycarbonyl.

12. A radiopharmaceutical kit for the preparation of an $^{18}$F-labelled tracer for use in PET, which comprises:
  (i) a vessel containing a compound of formula (I) or (Ia) as defined in claim 1; and
  (ii) means for eluting the vessel with a source of $^{18}$F$^-$;
  (iii) an ion-exchange cartridge for removal of excess $^{18}$F$^-$; and optionally
  (iv) a cartridge for solid-phase deprotection of the resultant product of formula (II) or (IIa) as defined in claim 1.

13. A cartridge for a radiopharmaceutical kit for the preparation of an $^{18}$F-labelled tracer for use in PET which comprises:
  (i) a vessel containing a compound of formula (I) as defined in claim 1; and
  (ii) means for eluting the vessel with a source of $^{18}$F$^-$.

* * * * *